United States Patent [19]

Fujii et al.

[11] 4,379,764
[45] Apr. 12, 1983

[54] PHENYLALANYLARGININE DERIVATIVES, PROCESS FOR PRODUCING SAME AND METHOD FOR MEASURING ACTIVITY OF ENZYMES USING SAME

[75] Inventors: Setsuro Fujii, Toyonaka; Mamoru Sugimito, Sakura; Takashi Yaegashi, Funabashi, all of Japan

[73] Assignee: Torii & Co. Ltd., Tokyo, Japan

[21] Appl. No.: 300,416

[22] Filed: Sep. 9, 1981

[30] Foreign Application Priority Data

Sep. 16, 1980 [JP] Japan .................................. 55-128270

[51] Int. Cl.³ .......................................... C07C 103/52
[52] U.S. Cl. .............................................. 260/112.5 R
[58] Field of Search .................................. 260/112.5 R

[56] References Cited

U.S. PATENT DOCUMENTS

| | | | |
|---|---|---|---|
| 4,137,225 | 1/1979 | Kenstam et al. | 260/112.5 R |
| 4,217,269 | 8/1980 | Cole | 260/112.5 R |
| 4,234,477 | 11/1980 | Fiedler | 260/112.5 R |
| 4,252,715 | 2/1981 | Aurell et al. | 260/112.5 R |

*Primary Examiner*—Delbert R. Phillips
*Attorney, Agent, or Firm*—Beveridge, DeGrandi, Kline

[57] ABSTRACT

A phenylalanylarginine derivative represented by the formula,

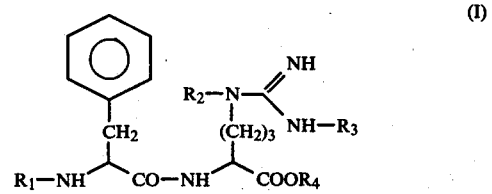

wherein $R_1$ represents hydrogen or an amino-protecting group; $R_2$ and $R_3$ represent hydrogen or guanidino-protecting groups; $R_4$ represents naphthyl. The above compound is useful as an excellent substrate for various enzymes, such as trypsin, plasmin, kallikrein, urokinase, Cl-esterase and the like. Accordingly, the activity of enzymes can be measured by use of said compound as a substrate.

7 Claims, 1 Drawing Figure

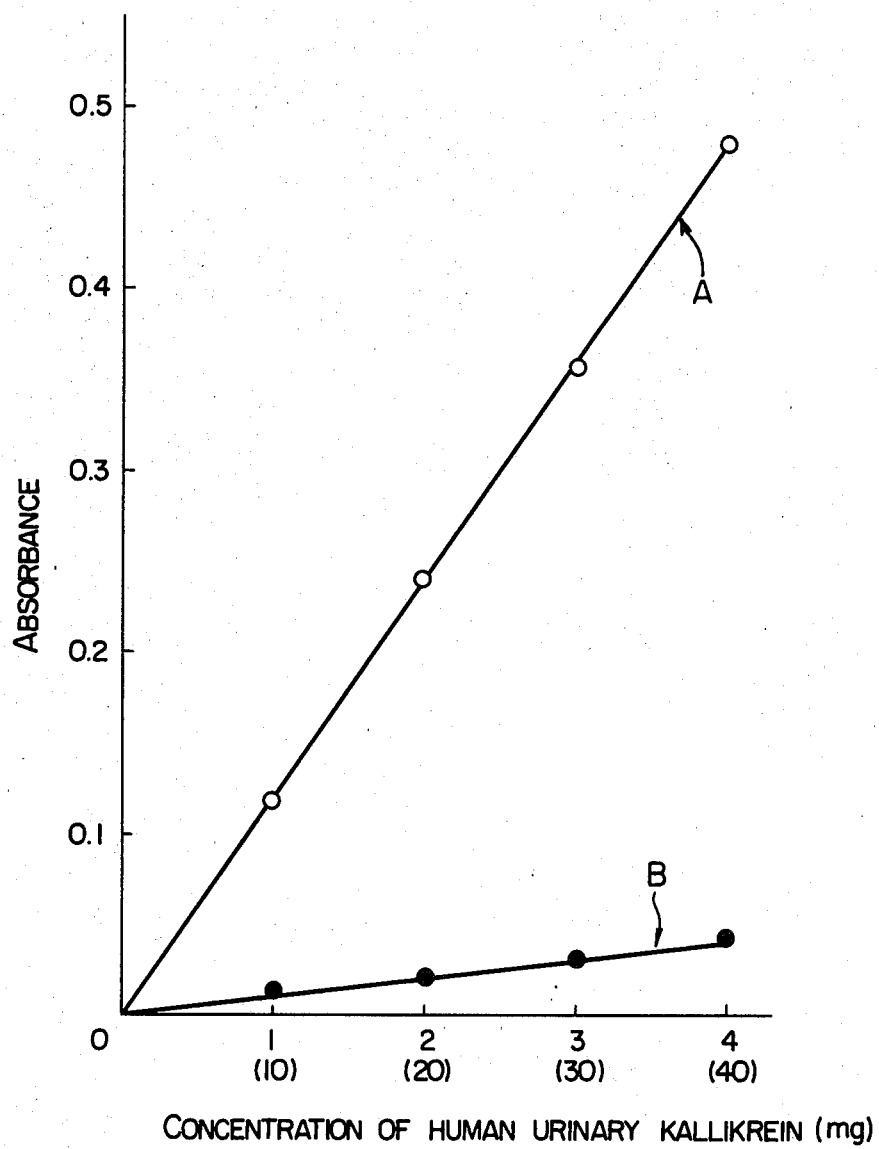

PHENYLALANYLARGININE DERIVATIVES, PROCESS FOR PRODUCING SAME AND METHOD FOR MEASURING ACTIVITY OF ENZYMES USING SAME

This invention relates to a phenylalanylarginine derivative, a process for producing the same and a method for measuring the activity of enzymes using the compound as a substrate.

Hitherto, many methods have been known for measuring the activity of enzymes. One of them is a method by which an alkyl ester of an amino acid is contacted as a substrate with an enzyme and the activity of the enzyme is determined from the degree of hydrolysis of the alkyl ester. For example, the well-known Hestrin method is one of the methods. This is a method which comprises contacting an enzyme with an alkyl ester of an amino acid, converting the remaining ester group after a given period of time with hydroxylamine into a hydroxamic acid, allowing it to react with ferric chloride to develop a color, and measuring the color as an absorbance, and determining the enzyme's ability to hydrolyze the ester, namely, the activity of enzyme, from the absorbance.

In addition, there is a method in which paranitroanilide of amino acid is used as a substrate and the ability to hydrolyze the same is used as an index, or the like. In these methods, a considerable amount of an enzyme is required, and when the enzyme concentration is low, or when the enzyme has a low activity, it has been difficult to measure the activity of enzyme. The present inventors have conducted extensive research on compounds satisfying the following three conditions: they have an affinity to an enzyme, the determination of the amount thereof is easy, and the detection sensitivity thereof is good. Consequently, the inventors have found compounds useful as substrate which are very excellent as to the above conditions as compared with the conventional ones and a simple method for measuring the activity of enzyme by use of the compounds.

An object of this invention is to provide a novel amino acid derivative which is useful as an excellent substrate for an enzyme.

Another object of this invention is to provide a process for producing the said novel amino acid derivative.

A further object of this invention is to provide a method for measuring the activity of an enzyme by using said novel amino acid derivative as a substrate for the enzyme.

Other objects and advantages of this invention will become apparent from the following description.

According to this invention, there is provided a phenylalanylarginine derivative represented by the formula,

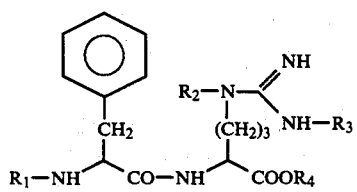

(I)

wherein $R_1$ is hydrogen or an amino-protecting group; $R_2$ and $R_3$ are hydrogen or guanidino-protecting groups; and $R_4$ is naphthyl.

This invention further provides a process for producing a phenylalanylarginine derivative represented by the formula (I), which comprises subjecting to dehydration-condensation a compound (II) represented by the formula,

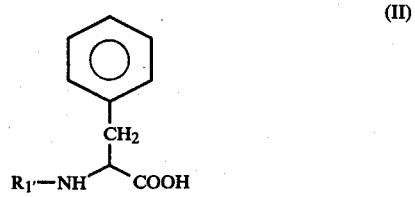

(II)

wherein $R_{1'}$ represents an amino-protecting group, and an arginine derivative (III) represented by the formula,

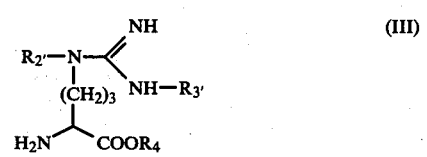

(III)

wherein $R_{2'}$ and $R_{3'}$ are guanidino-protecting groups and $R_4$ has the same meaning as defined above, in a conventional manner to obtain a compound (IV) represented by the formula,

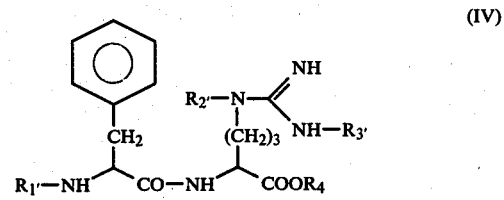

(IV)

wherein $R_{1'}$, $R_{2'}$, $R_{3'}$ and $R_4$ have the same meanings as defined above, and then removing, if necessary, the amino-protecting group and/or the guanidino-protecting group from the compound (IV) in a conventional manner.

According to this invention, there is further provided a method for measuring the activity of an enzyme which comprises contacting a phenylalanylarginine derivative represented by the formula (I) as a substrate with the enzyme.

In the formulas (I), (II), (III) and (IV), the amino-protecting group includes protecting groups which are conventionally used in the synthesis of a peptide, such as t-butyloxycarbonyl, benzyloxycarbonyl, acetyl, benzoyl, tosyl and the like, among which acetyl and benzoyl are preferred. The guanidino-protecting group includes protecting groups which are conventionally used in the synthesis of a peptide, such as nitro, tosyl, benzyloxycarbonyl or the like, or the guanidino group may form an acid-addition salt by proton-addition. Among them, benzyloxycarbonyl is preferred.

The starting compound (II) used in the production of the compound (I) of this invention may be any commercially available one.

The starting arginine derivative (III) includes $N^\delta, N^\omega$-dibenzyloxycarbonyl-L-arginine 1-naphthyl ester trifluoroacetate, and the like, and may be prepared by naphthylating an arginine derivative (III′) having suitable protecting group represented by the formula,

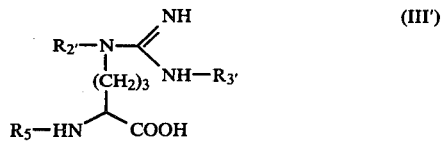

wherein $R_{2'}$ and $R_{3'}$ have the same meanings as defined above, and $R_5$ represents an amino-protecting group different from the $R_{2'}$ and $R_{3'}$ groups, to form a compound (III″) represented by the formula,

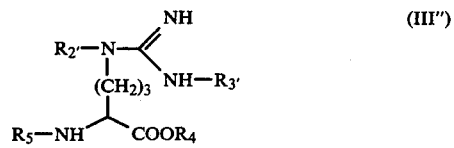

wherein $R_{2'}$, $R_{3'}$, $R_4$ and $R_5$ have the same meanings as defined above, and then selectively removing only the amino-protecting group in the α-position from the compound (III″).

In the production of the compound (IV), the compound (II) and the arginine derivative (III) are dissolved in a suitable solvent, and to the resulting solution is added an activating agent which is usually used, such as dicyclohexylcarbodiimide (DCC), diphenylphosphorylazide (DPPA), an alkyl chlorocarbonate or the like, after which, if necessary, a base such as triethylamine or the like, is added thereto and the resulting mixture is stirred, thereby preparing the compound (IV). The solvent used includes conventional solvents such as chloroform, dichloromethane, dimethylformamide, tetrahydrofuran and the like as far as the starting materials can be dissolved therein. The reaction temperature may be within the range of 0° to 40° C.

After the completion of the reaction, the compound (IV) can be isolated from the reaction mixture by a conventional treatment. That is to say, when DCC is used as the activating agent, the dicyclohexylurea (DCU) precipitated is removed by filtration, and a suitable extracting solvent such as ethyl acetate is added to the filtrate, after which the extract is washed with an aqueous citric acid solution, saturated aqueous sodium bicarbonate solution or saturated aqueous sodium chloride solution, dried over anhydrous magnesium sulfate, and then evaporated under reduced pressure to remove the solvent, thereby obtaining the compound (IV).

The amino-protecting group and/or the guanidino-protecting group of the compound (IV) is removed in a conventional manner. That is to say, when the amino-protecting group and the guanidino-protecting group are benzyloxycarbonyl, the compound (IV) is dissolved in a suitable solvent and a catalyst such as palladium-carbon or the like is added to the resulting solution to remove the protecting group reductively, or the compound (IV) is added to a solution of hydrobromic acid in acetic acid and the hydrobromide of the objective compound precipitated is taken out by filtration, whereby the compound (I) is obtained.

The compound (I) of this invention is useful as an excellent substrate for various enzymes such as trypsin, plasmin, kallikrein, urokinase, Cl-esterase, thrombin and the like. That is to say, when the compound (I) of this invention is contacted with an enzyme, the compound serves as a substrate, and naphthol is liberated by hydrolysis with the enzyme after a given period of time, after which the amount of the naphthol is measured to determine the activity of the enzyme. The fact that the activity of an enzyme can be measured easily is very important for quantitative analysis of an enzyme preparation, diagnosis by measuring the enzyme pattern in blood, diagnosis by measuring the enzyme concentration in blood or urine, or the like.

When the activity of an enzyme is measured according to the method of this invention, the enzyme is contacted with a given amount of the compound (I) of this invention in a suitable buffer solution, and after a given period of time at a given temperature, the amount of naphthol liberated is measured, thereby determining the activity of the enzyme. The buffer solution may be a suitable one having the optimum pH for the enzyme. The reaction may be effected under suitable constant conditions as to temperature and time, though it is preferable to measure the amount of the naphthol liberated at a temperature of 25° to 37° C. after 30 min.

The measurement of the amount of naphthol may be conducted by any of the known methods, for example, a physicochemical method, such as, gas chromatography, thin layer chromatography, or the like; or a chemical method, such as, ferric chloride reaction, diazo-coupling reaction, a Fast Violet B salt (FVB) method, or the like, though a method which comprises adding FVB to the reaction mixture to develop a color and measuring the absorbance by means of a photometer is more preferable in view of simplicity and detection sensitivity.

When the activity of an enzyme is measured using acetyl-L-phenylalanyl-L-arginine 1-naphthyl ester as a substrate, the detection sensitivity is higher than when the activity is measured using Nα-benzoyl-L-arginine ethyl ester or Nα-tosyl-L-arginine methyl ester (TAME), which has hitherto been known as a substrate for enzymes, according to the Hestrin method, and in particular, the acetyl-L-phenylalanyl-L-arginine 1-naphthyl ester has a detection sensitivity to kallikrein about 105 times that of Nα-benzoyl-L-arginine ethyl ester or Nα-tosyl-L-arginine methyl ester.

The amount of the naphthol measured by said method corresponds to the activity or amount of the enzyme.

According to the process of this invention, a change in enzyme concentration in blood or urine due to various diseases can easily be detected. For example, there is a relationship between essential hypertension and the kallikrein concentration in urine of a hypertensive, and it is said that essential hypertension may be diagnosed by measuring the kallikrein concentration. Hitherto, the following methods for measuring the kallikrein concentration in urine have been known:

1. Assay of TAME (Tohoku J. Med., 116 (1975) by Masahide Seino)
2. Bioassay (Tohoku J. Exp. Med., 87 (1965) by Keishi Abe)
3. Radioimmunoassay.

These are complicated in operation, and the results obtained greatly fluctuate. In addition, the methods are expensive and often inconvenient for clinical examination. However, when the compound (I) of this invention is used, the kallikrein concentration in urine can be determined from a small amount of urine by a simple operation.

The method for measuring the activity of an enzyme of this invention can be applied to not only a single enzyme-containing system but also a system containing various enzyme. That is to say, the measurement of the enzyme pattern in urine or blood has been interesting for diagnosis of disease, but conventional methods have not been so often conducted because of their complexities. However, with this invention, their complexities have been cleared. When, for example, the activity of an enzyme contained in urine is measured, an enzyme pattern in urine which has never been seen has been made possible to see by adding urine on a suitable supporter, separating enzymes therefrom by electro-phoresis or the like, immersing the enzymes in an aqueous solution of the compound (I) of this invention for a suitable period of time, and then adding the above-mentioned color developing agent thereto.

This invention is further illustrated below referring to Examples and the accompanying drawings showing standard curves of the concentration of human urinary kallikrein, in which the ordinate indicates absorbance and the abscissa indicates the amount (mg) of kallikrein, provided that the numbers in the parentheses refer to the amounts of kallikrein in the case of Nα-tosylarginine methyl ester. Curve A refers to the standard curve obtained by the method of Example 4, and Curve B to the standard curve obtained by the method of the Comparative Example.

EXAMPLE 1

Production of L-phenylalanyl-L-arginine 1-naphthyl ester dihydrochloride

In 8 ml of dimethylformamide (DMF) were dissolved 898 mg of benzyloxycarbonyl-L-phenylalanine and 2.05 g of $N^\delta,N^\omega$-dibenzyloxycarbonyl-L-arginine 1-naphthyl ester trifluoroacetate, and to the resulting solution were added 681 mg of dicyclohexylcarbodiimide (DCC), 405 mg of 1-hydroxybenzotriazole (HOBt) and 304 mg of triethylamine (TEA) with ice-cooling and with stirring, after which the mixture was stirred for 3 hrs at the same temperature. The temperature was elevated to room temperature and the mixture was stirred for a further 24 hrs. After the reaction, the crystals of dicyclohexylurea (DCU) precipitated were removed by filtration, and ethyl acetate was added to the filtrate, after which the mixture was washed with 10% aqueous citric acid solution, saturated sodium bicarbonate solution and saturated sodium chloride solution in this order, dried over anhydrous magnesium sulfate, and thereafter evaporated under reduced pressure to removed the solvent. The white powder thus precipitated was collected and recrystallized from chloroform-diethyl ether to obtain 1.1 g (yield 43%) of benzyloxycarbonyl-L-phenylalanyl-$N^\delta,N^\omega$-dibenzyloxycarbonyl-L-arginine 1-naphthyl ester, m.p. 125°–130° C.

IR $\nu_{max}^{KBr}$ cm$^{-1}$: 3380, 3280, 1750, 1720, 1650.
NMR δ ppm (CDCl$_3$): 1.6–2.2 (4H, b, >N—CH$_2$CH$_2$CH$_2$CH<),

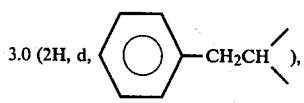

3.8–4.2 (2H, b, >N—CH$_2$CH$_2$—), 4.4–5.0 (2H, b, —CH × 2), 5.0, 5.1, 5.3 each

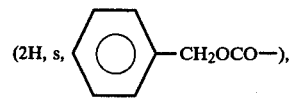

7.1–8.0 (27H, m, aromatic protons).

In DMF was dissolved 935 mg of the above ester, and to the resulting solution were added 0.5 g of 10% palladium-carbon (Pd-C) and 0.98 ml of a 2 N hydrochloric acid-dioxane solution, after which hydrogen gas was passed through the resulting mixture with ice-cooling and with stirring for 4 hrs. After the reaction, the Pd-C was removed by filtration, and 300 ml of anhydrous diethyl ether was added dropwise to the filtrate, upon which a powder was precipitated. The powder was collected by filtration to obtain 450 mg (yield 78%) of L-phenylalanyl-L-arginine 1-naphthyl ester dihydrochloride, m.p. 215° C. (decomp.).

IR $\nu_{max}^{KBr}$ cm$^{-1}$: 3380, 3180, 1740, 1650.
NMR δ ppm (DMSO-d$_6$): 1.6–2.2 (4H, b, >N—CH$_2$CH$_2$CH$_2$CH<),

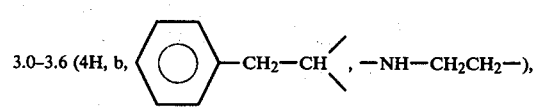

4.0–4.5, 4.5–4.9 each (1H, b, —CH), 7.1–8.7 (12H, m, aromatic protons).

EXAMPLE 2

Production of acetyl-L-phenylalanyl-L-arginine 1-naphthyl ester hydrochloride

In 15 ml of DMF were dissolved 2.07 g of acetyl-L-phenylalanine and 6.80 g of $N^\delta,N^\omega$-dibenzyloxycarbonyl-L-arginine 1-naphthyl ester trifluoroacetate, after which 2.27 g of DCC, 1.35 g of HOBt and 1.01 g of TEA were added to the resulting solution with ice-cooling and stirred for 3 hrs. The temperature thereof was thereafter elevated to room temperature, and the mixture was stirred for a further 24 hrs at room temperature. After the reaction, the DCU thus precipitated was removed by filtration, and ethyl acetate was added to the filtrate, and the resulting mixture was washed with 10% citric acid solution, saturated sodium bicarbonate solution and saturated sodium chloride solution in this order, dried over anhydrous magnesium sulfate and then evaporated under reduced pressure to remove the solvent. The residue was recrystallized from chloroform-diethyl ether to obtain 5.55 g (yield 73%) of white powder, m.p. 179°–179.5° C., which was acetyl-L-phenylalanyl-$N^\delta,N^\omega$-dibenzyloxycarbonyl-L-arginine 1-naphthyl ester.

IR $\nu_{max}^{KBr}$ cm$^{-1}$: 3380, 3260, 1750, 1720, 1640
NMR δ ppm (CDCl$_3$): 1.6–2.2 (4H, b, >N—CH$_2$CH$_2$CH<), 1.8 (3H, s, CH$_3$CONH—), 3.0 (2H, d, 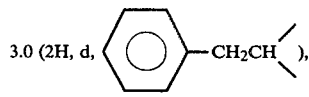), 3.8–4.2 (2H, b, >N—CH₂CH₂—), 4.7–5.0

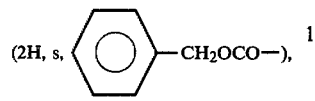
(2H, b, \CH × 2), 5.12, 5.21 each (2H, s, 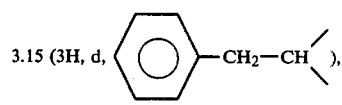), 7.0–8.0 (22H, m, aromatic protons).

In 100 ml of DMF was dissolved 5.3 g of the above ester, after which 3.0 g of 10% Pd-C and 7.0 ml of 2 N hydrochloric acid-dioxane solution were added to the resulting solution. The resulting mixture was stirred with ice-cooling for 6 hrs while passing hydrogen gas therethrough. After the reaction, the Pd-C was removed by filtration, and anhydrous diethyl ether was added to the filtrate, upon which an oily substance was precipitated. The supernatant was removed by decantation, and anhydrous diethyl ether was added again to the residue, and the mixture was stirred to obtain 3.1 g (yield 84%) of white powder, m.p. 115° C. (decomp.), which was acetyl-L-phenylalanyl-L-arginine 1-naphthyl ester hydrochloride.

IR $\nu_{max}^{KBr}$ cm$^{-1}$: 3250, 1750, 1650.

NMR δ ppm (CDCl₃): 1.6–2.2 (4H, b, >N—CH₂CH₂CH₂CH<), 3.2 (3H, d, 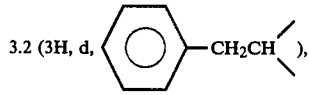), 3.8–4.2 (2H, b, >N—CH₂CH₂—), 4.8–5.1

(2H, b, \CH × 2), 5.1, 5.2 each (2H, s, 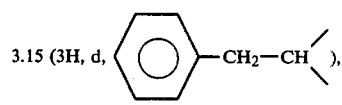), 7.1–7.9 (27H, m, aromatic protons).

EXAMPLE 3

Production of benzoyl-L-phenylalanyl-L-arginine 1-naphthyl ester hydrochloride

In 8 ml of DMF were dissolved 808 mg of benzoyl-L-phenylalanine and 2.05 g of N$^\delta$,N$^\omega$-dibenzyloxycarbonyl-L-arginine 1-naphthyl ester trifluoroacetate, after which 681 mg of DCC, 405 mg of HOBt and 304 mg of TEA were added thereto with ice-cooling, and the mixture was stirred for 3 hrs, and then at room temperature for a further 24 hrs. After the reaction, the DCU thus precipitated was removed by filtration, and ethyl acetate was added to the filtrate, after which the mixture was washed with 10% citric acid solution, saturated sodium bicarbonate solution and saturated sodium chloride solution in this order, and then dried over anhydrous magnesium sulfate. The solvent was removed by evaporation under reduced pressure, and the residue thus obtained was recrystallized from chloroform-diethyl ether to obtain 1.4 g (yield 57%) of benzoyl-L-phenylalanyl-N$^\delta$,N$^\omega$-dibenzyloxycarbonyl-L-arginine 1-naphthyl ester, m.p. 177°–185° C.

IR $\nu_{max}^{KBr}$ cm$^{-1}$: 3380, 3270, 1750, 1720, 1630.

NMR δ ppm (CDCl₃): 1.6–2.2 (4H, b, >N—CH₂—CH₂—CH₂—CH<), 3.15 (3H, d, 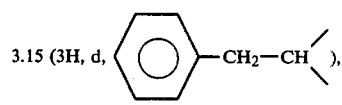), 3.8–4.2 (2H, b, >N—CH₂—CH₂—), 4.8–5.1

(2H, b, \CH × 2), 5.1, 5.2 each (2H, s, 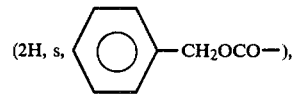), 7.1–7.9 (27H, m, aromatic protons).

In 10 ml of DMF was dissolved 1.07 g of the above ester, after which 0.5 g of 10% Pd-C and 1.65 ml of 2 N hydrochloric acid-dioxane solution were added thereto. The mixture was stirred with ice-cooling for 3 hrs while passing hydrogen gas therethrough. After the reaction, the reaction mixture was filtered to remove the Pd-C, and 500 ml of anhydrous diethyl ether was added to the filtrate. The white powder thus precipitated was collected and vacuum-dried over P₂O₅ at 110° C. for 3 hrs to obtain 700 mg (yield 92%) of benzoyl-L-phenylalanyl-L-arginine 1-naphthyl ester hydrochloride, m.p. 112° C.-(decomp.).

IR $\nu_{max}^{KBr}$ cm$^{-1}$: 3250, 1750, 1640.

NMR δ ppm (DMSO-d₆): 1.6–2.2 (4H, b, >N—CH₂—CH₂CH₂CH<), 3.0–3.5 (4H, b, 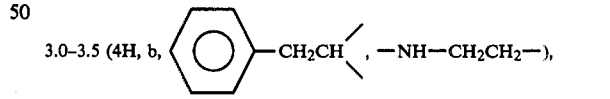), 4.5–5.0 (2H, b, \CH × 2), 7.1–8.0 (17H, m, aromatic protons).

EXAMPLE 4

Measurement of the activity of kallikrein by use of acetyl-L-phenylalanyl-L-arginine 1-naphthyl ester as substrate To 1.7 ml of 50 mM phosphate buffer solution (pH 7.0) were added 0.1 ml of human urinary kallikrein at various concentrations and 0.2 ml of 1.0 mM aqueous solution of acetyl-L-phenylalanyl-L-arginine 1-naphthyl ester, after which the mixture was subjected to incubation at 25° C. for 30 min. To the mixture was added 20 microliters of 8% sodium laurysulfate solution and the resulting mixture was cooled with iced water. To the mixture was added 0.2 ml of a 1% Fast Violet B salt (FVB) solution, and the mixture was allowed to stand at 0° C. for 10 min, after which 2 ml of glacial acetic acid was added. The color thus developed was measured as absorbance (505 nm) by means of a spectrophotometer to determine the amount of the naphthol liberated by hydrolysis with the enzyme. As a control, 0.1 ml of the above buffer solution free from kallikrein was substituted for the mixture of the buffer solution and the kallikrein. The amount of the naphthol liberated corresponded to the activity of the enzyme.

The results obtained at each kallikrein concentration by the above method are shown by Curve A in the accompanying drawings.

COMPARATIVE EXAMPLE

Measurement of the activity of kallikrein by use of Nα-tosyl-L-arginine methyl ester as substrate To 0.5 ml of human urinary kallikrein were added 0.4 ml of Nα-tosylarginine methyl ester solution (10 micromoles/0.4 ml of 5% DMSO) and 0.1 ml of 100 mM phosphate buffer solution (pH 7.4). The mixture was subjected to incubation at 37° C. for 30 min, and 1.5 ml of hydroxylamine solution (a mixture of equal amounts of 2 M NH$_2$OH hydrochloride and 3.5 M NaOH) was added thereto, after which the mixture was allowed to stand at room temperature for 15 min. Thereto were added 1 ml of 18% by weight trichloroacetic acid solution, 1 ml of 4 N hydrochloric acid and 1 ml of 10% by weight ferric chloride solution, and the resulting mixture was stirred thoroughly and then centrifuged at 3,000 r.p.m. for 10 min. The color developed in the supernatant was measured as absorbance (530 nm) by means of a spectrophotometer. The value obtained corresponds to the amount of the substrate remaining unhydrolyzed with kallikrein, and therefore, the activity of the enzyme corresponds to the difference between the value obtained when no enzyme was used (control) and the value obtained after the enzyme reaction.

The results obtained at each kallikrein concentration by the above method are shown by Curve B in the accompanying drawings.

What is claimed is:

1. A phenylalanylarginine derivative represented by the formula,

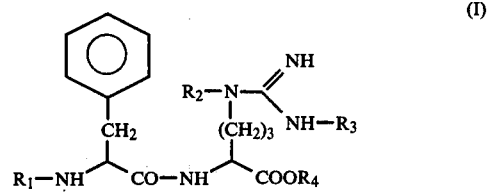

wherein $R_1$ represents hydrogen or an amino-protecting group; $R_2$ and $R_3$ represent hydrogen or guanidino-protecting groups; and $R_4$ represents naphthyl.

2. A phenylalanylarginine derivative according to claim 1, wherein $R_1$ is hydrogen.

3. A phenylalanylarginine derivative according to claim 1, wherein $R_1$ is acetyl, benzoyl or benzyloxycarbonyl.

4. A phenylalanylarginine derivative according to claim 2 or 3, wherein $R_2$ and $R_3$ represent hydrogen or benzyloxycarbonyl.

5. L-phenylalanyl-L-arginine 1-naphthyl ester.

6. Benzoyl-L-phenylalanyl-L-arginine 1-naphthyl ester.

7. Acetyl-L-phenylalanyl-L-arginine 1-naphthyl ester.

* * * * *